US011432753B2

(12) United States Patent
Alam et al.

(10) Patent No.: US 11,432,753 B2
(45) Date of Patent: Sep. 6, 2022

(54) PARALLEL IMPLEMENTATION OF DEEP NEURAL NETWORKS FOR CLASSIFYING HEART SOUND SIGNALS

(71) Applicant: Tata Consultancy Services Limited, Mumbai (IN)

(72) Inventors: Shahnawaz Alam, Kolkata (IN); Rohan Banerjee, Kolkata (IN); Soma Bandyopadhyay, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 672 days.

(21) Appl. No.: 16/534,955

(22) Filed: Aug. 7, 2019

(65) Prior Publication Data

US 2020/0046244 A1 Feb. 13, 2020

(30) Foreign Application Priority Data

Aug. 8, 2018 (IN) .............................. 201821029768

(51) Int. Cl.
*G06K 9/62* (2022.01)
*A61B 5/316* (2021.01)
(Continued)

(52) U.S. Cl.
CPC .............. *A61B 5/316* (2021.01); *A61B 5/349* (2021.01); *A61B 5/7264* (2013.01); *G06N 3/0454* (2013.01)

(58) Field of Classification Search
CPC ......... A61B 5/02; A61B 5/0006; A61B 5/316; A61B 5/318; A61B 5/346; A61B 5/349;
(Continued)

(56) References Cited

U.S. PATENT DOCUMENTS

2015/0157273 A1\* 6/2015 An ....................... A61B 5/7275
600/595
2016/0354053 A1\* 12/2016 Tsai ..................... A61B 5/0803
(Continued)

FOREIGN PATENT DOCUMENTS

CN 108143407 A 6/2018

OTHER PUBLICATIONS

Latif et al. ("Abnormal Heartbeat Detection Using Recurrent Neural Networks", arXiv:1801.08322v1 [cs.CV] Jan. 25, 2018, 8 pages) (Year: 2018).\*

*Primary Examiner* — Duy M Dang
(74) *Attorney, Agent, or Firm* — Finnegan, Henderson, Farabow, Garrett & Dunner, LLP

(57) ABSTRACT

Conventional systems and methods of classifying heart signals include segmenting them which can fail due to the presence of noise, artifacts and other sounds including third heart sound 'S3', fourth heart sound 'S4', and murmur. Heart sounds are inherently prone to interfering noise (ambient, speech, etc.) and motion artifact, which can overlap time location and frequency spectra of murmur in heart sound. Embodiments of the present disclosure provide parallel implementation of Deep Neural Networks (DNN) for classifying heart sound signals (HSS) wherein spatial (presence of different frequencies component) filters from Spectrogram feature(s) of the HSS are learnt by a first DNN while time-varying component of the signals from MFCC features of the HSS are learnt by a second DNN for classifying the heart sound signal as one of normal sound signal or murmur sound signal.

18 Claims, 4 Drawing Sheets

(51) Int. Cl.
*A61B 5/00* (2006.01)
*G06N 3/04* (2006.01)
*A61B 5/349* (2021.01)

(58) Field of Classification Search
CPC ... A61B 5/7253; A61B 5/7257; A61B 5/7264;
A61B 5/7267; A61B 8/00; A61B 8/02;
G16H 50/00; G16H 50/20; G06N 3/0454;
G06N 20/00; G06V 10/40; G06V 30/18;
G06V 30/187; G06V 30/191; G06T
2207/10132; G06T 2207/20; G06T
2207/20021; G06T 2207/20056; G06T
2207/30004; G06T 2207/30048; G06T
2207/20081; G06T 2207/20084
See application file for complete search history.

(56) References Cited

U.S. PATENT DOCUMENTS

| | | |
|---|---|---|
| 2018/0108440 A1 | 4/2018 | Stevens et al. |
| 2018/0116597 A1 | 5/2018 | Yu et al. |

\* cited by examiner

PARALLEL IMPLEMENTATION OF DEEP NEURAL NETWORKS FOR CLASSIFYING HEART SOUND SIGNALS

PRIORITY CLAIM

This U.S. patent application claims priority under 35 U.S.C. § 119 to: India Application No. 201821029768, filed on Aug. 8, 2018. The entire contents of the aforementioned application are incorporated herein by reference.

TECHNICAL FIELD

The disclosure herein generally relates to classification systems, and, more particularly, to parallel implementation of deep neural networks for classifying heart sound signals (HSS).

BACKGROUND

Cardiovascular diseases (CVDs) continue to be the leading cause of mortality and morbidity worldwide. Cardiac auscultation using stethoscope has been a classic procedure for screening heart abnormalities. Heart sound (Phonocardiogram—PCG) auscultation though being noninvasive and inexpensive to capture, have limitations: dependency on hearing sense to judge unbiasedly, variation in a medical inference of individual examiner, and precise skill which takes years of experience to gain, therefore, are not fully reliable. However, digital signal processing of PCG has shown a high correlation with the evaluation of cardiac defects and primary healthcare, which makes it a popular choice. Therefore, intelligent agent over auscultation would assist medical practitioners with decision support abilities.

Heart sounds consist of two primary and fundamental heart sound or beats, S1 and S2 (sounds like 'lub' and 'dub'), occurring sequentially one after another. A single mechanical cycle of heart, or cardiac cycle, produces a S1 sound when the closing of the mitral and tricuspid valves occur followed by Systole then a S2 sound by the closing of the pulmonary and aortic valves followed by Diastole. The ideal blood flow in the heart is streamlined; thus keeping interbeat sounds to minimal. However, turbulence in the blood flow due to structural defects and other diseases in the heart creates vibration in the surrounding tissue, thus creating audible noise, called pathologic murmur. Murmurs have diverse frequency ranges of sound compared to S1 and S2 and depending on their nature they can be as high as 600 Hz. Murmurs are one of the pathological indicators of abnormalities in the heart, which needs medical attention. Functional, or innocent murmurs are caused due to physiologic conditions outside the heart.

Murmurs, depending upon the position in the cardiac cycle can be further classified into systolic and diastolic murmurs; however, they quickly get mixed up with cardiac beats which makes it difficult to identify by human hearing sense and thereby leads to inaccurate classification of heart sound signals.

SUMMARY

Embodiments of the present disclosure present technological improvements as solutions to one or more of the above-mentioned technical problems recognized by the inventors in conventional systems. For example, in one aspect, there is provided a processor implemented method for classifying heart sound signals. The method comprises receiving, via a neural network architecture system, a plurality of heart sound signals specific to one or more users, wherein each heart sound signal from the plurality of heart sound signal is unique and pertains to a corresponding user from the one or more users; splitting the plurality of heart sound signals into a plurality of windows, wherein each of the plurality of windows is of a fixed time duration; extracting a set of frequency domain based spectrogram features and a set of time domain based Mel Frequency Cepstral Coefficient (MFCC) features from each of the plurality of windows; concurrently inputting the set of MFCC features to a first Deep Neural Network and the set of spectrogram features to a second Deep Neural Network respectively; concurrently learning (i) a temporal behavior by the first Deep Neural Network based on the set of time based Mel Frequency Cepstral Coefficient (MFCC) features and (ii) a spatial behavior by the second Deep Neural Network based on the set of frequency based spectrogram features; concatenating the learned temporal behavior and the learned spatial behavior to obtain a concatenated behavioral set; and classifying, using a plurality of fully connected layers and a softmax layer associated with the neural network architecture system, the plurality of heart sound signals as at least one of a normal sound signal or a murmur sound signal based on the concatenated behavioral set, wherein during the learning of the temporal behavior and the spatial behavior, one or more weights and biases of (i) one or more layers of the first DNN and the second DNN respectively, (ii) the plurality of fully connected layers and the softmax layer of the neural network architecture system are learnt.

In an embodiment, the method may further comprise receiving, via the neural network architecture system, a test heart sound signal; extracting one or more spectrogram features and one or more MFCC features from the test heart sound signal; applying the learned one or more weights and biases on the one or more spectrogram features and the one or more MFCC features to obtain a plurality of probabilities pertaining to the test heart sound signal; and classifying, based on the plurality of probabilities, the test heart sound signal as the normal sound signal or a murmur sound signal.

In an embodiment, the first Deep Neural Network and the second Deep Neural Network are different from each other wherein the first Deep Neural Network comprises a Recurrent Neural Network and the second Deep Neural Network comprises a Convolution Neural Network.

In another aspect there is provided a Neural Network architecture system for classifying heart sound signals. The system comprises: a memory storing instructions; one or more communication interfaces; and one or more hardware processors coupled to the memory via the one or more communication interfaces, wherein the one or more hardware processors are configured by the instructions to: receive a plurality of heart sound signals specific to one or more users, wherein each heart sound signal from the plurality of heart sound signal is unique and pertains to a corresponding user from the one or more users; split the plurality of heart sound signals into a plurality of windows, wherein each of the plurality of windows is of a fixed time duration; extract a set of frequency domain based spectrogram features and a set of time domain based Mel Frequency Cepstral Coefficient (MFCC) features from each of the plurality of windows; concurrently input the set of MFCC features to a first Deep Neural Network and the set of spectrogram features to a second Deep Neural Network respectively. In an embodiment, the first Deep Neural Network and the second Deep Neural Network are configured by the instructions to: concurrently learn a temporal behavior based on the set of time based Mel Frequency Cepstral Coefficient (MFCC) features and (ii) a spatial behavior based on the set of frequency based spectrogram features respectively, wherein the learned temporal behavior and the learned spatial behavior are concatenated to obtain a concatenated behavioral set based on which the plurality of heart sound signals are classified as at least one of a normal sound signal or a murmur sound signal, using a plurality of fully connected layers and a softmax layer associated with the neural network architecture system. In an embodiment, during the learning of the temporal behavior and the spatial behavior, one or more weights and biases of (i) one or more layers of the first DNN and the second DNN respectively, (ii) the plurality of fully connected layers and the softmax layer of the neural network architecture system are learnt.

In an embodiment, the neural network architecture system is further configured by the instructions to: receive a test heart sound signal; extract one or more spectrogram features and one or more MFCC features from the test heart sound signal; apply the learned one or more weights and biases on the one or more spectrogram features and the one or more MFCC features to obtain a plurality of probabilities pertaining to the test heart sound signal; and classify, based on the plurality of probabilities, the test heart sound signal as the normal sound signal or a murmur sound signal.

In an embodiment, the first Deep Neural Network and the second Deep Neural Network are different from each other wherein the first Deep Neural Network comprises a Recurrent Neural Network and the second Deep Neural Network comprises a Convolution Neural Network.

In yet another aspect, there are provided one or more non-transitory machine readable information storage mediums comprising one or more instructions which when executed by one or more hardware processors causes classifying heart sound signals. The instructions comprise receiving, via a neural network architecture system, a plurality of heart sound signals specific to one or more users, wherein each heart sound signal from the plurality of heart sound signal is unique and pertains to a corresponding user from the one or more users; splitting the plurality of heart sound signals into a plurality of windows, wherein each of the plurality of windows is of a fixed time duration; extracting a set of frequency domain based spectrogram features and a set of time domain based Mel Frequency Cepstral Coefficient (MFCC) features from each of the plurality of windows; concurrently inputting the set of MFCC features to a first Deep Neural Network and the set of spectrogram features to a second Deep Neural Network respectively; concurrently learning (i) a temporal behavior by the first Deep Neural Network based on the set of time based Mel Frequency Cepstral Coefficient (MFCC) features and (ii) a spatial behavior by the second Deep Neural Network based on the set of frequency based spectrogram features; concatenating the learned temporal behavior and the learned spatial behavior to obtain a concatenated behavioral set; and classifying, using a plurality of fully connected layers and a softmax layer associated with the neural network architecture system, the plurality of heart sound signals as at least one of a normal sound signal or a murmur sound signal based on the concatenated behavioral set, wherein during the learning one or more weights and biases of (i) one or more layers of the first DNN and the second DNN respectively, (ii) the plurality of fully connected layers and the softmax layer of the neural network architecture system are learnt.

In an embodiment, the instructions which when executed by the one or more hardware processors may further comprise receiving, via the neural network architecture system, a test heart sound signal; extracting one or more spectrogram features and one or more MFCC features from the test heart sound signal; applying the learned one or more weights and biases on the one or more spectrogram features and the one or more MFCC features to obtain a plurality of probabilities pertaining to the test heart sound signal; and classifying, based on the plurality of probabilities, the test heart sound signal as the normal sound signal or a murmur sound signal.

In an embodiment, the first Deep Neural Network and the second Deep Neural Network are different from each other wherein the first Deep Neural Network comprises a Recurrent Neural Network and the second Deep Neural Network comprises a Convolution Neural Network.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
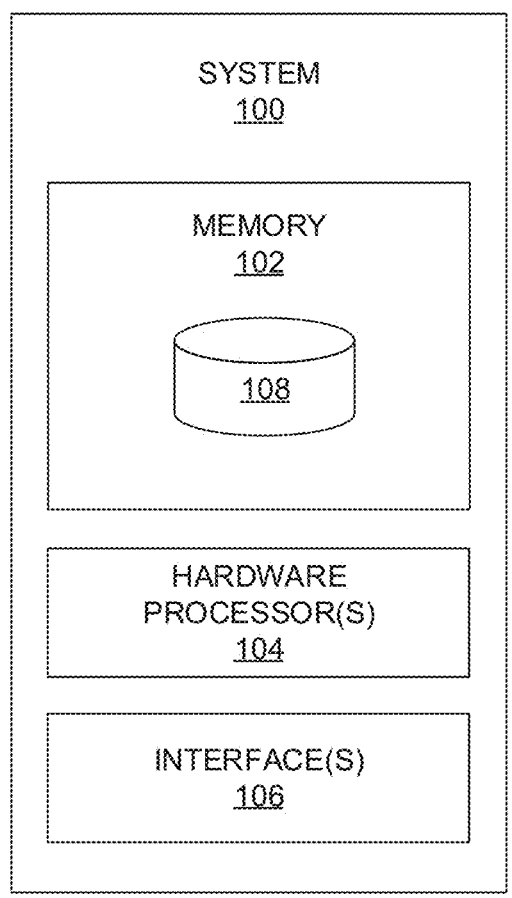
FIG. 1 illustrates an exemplary block diagram of a neural network architecture system for classifying heart sound signals (HSS) in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

In recent times, phonocardiogram (also known as PCG) murmur detection has been an active area of research, with various studies centering on the determination of a multitude of features extraction which correlates to murmur, mostly related to time, frequency, morphological, parametric modeling and spectral properties of heart sounds. In the past, the studies have shown that researchers have extracted features based on coefficients of wavelet packet decomposition to classify heart sound into physiological and pathological murmurs. Features were introduced to a neural network to get 85% accuracy. However, it does not provide information about the normal class or noisy recordings which may have a similar pattern in wavelet space, thus difficult to segregate. Conventional studies have taken instantaneous energy and frequency estimation (central finite difference frequency estimation and zero crossing frequency estimation) of heart sound for the classification. While few other studies have extracted wavelet-based features to discriminate normal and abnormal heart sound using modified Support Vector Machine (Least Square SVM)—which introduces Lagrange multiplier based on Least Mean Square algorithm. Few other studies have used perceptual and fractal features to understand the temporal patterns of the heart sound murmur, in which fractals have shown significant performance boost over other. The research has also indicated analyses of the systolic duration of heart sound using instantaneous frequency from averaged Wigner-Ville distribution for the characterization of PCG. As can be seen from above, previous studies have mostly focused on the feature extraction based method for classification. However, handcrafted features mostly (or may) fail in the on-field test environment, as these features are highly biased towards training dataset. Moreover, number of the prior studies for heart sound classification may lead to flaw(s) because of utilization of carefully-selected data, failure to use a variety of PCG recordings from different demographics and pathological conditions, training and evaluation on clean recordings, etc. There is a possibility that segmentation can fail miserably due to the presence of noise, artifacts and other sounds including third heart sound 'S3', fourth heart sound 'S4', and murmur. Heart sounds are inherently prone to interfering noise (ambient, speech, etc.) and motion artifact, which can overlap time location and frequency spectra of murmur in heart sound.

Murmur being mostly pseudo-periodic in nature (assuming noises are random and varying), spectral and temporal sequence analysis best suits the attempt for classification which adapts and tracks the statistical property of the signal over a time-frequency space. Embodiments of the present disclosure propose parallel implementation of deep neural networks for classifying heart sound signals. More particularly, the present disclosure implements parallel combination of the Recurrent Neural Network (RNN) based Bidirectional Long Short-Term Memory (BiLSTM) and Convolutional Neural Network (CNN) to learn visual and time-dependent characteristics of Murmur in PCG waveform. Acoustic features set are presented to the proposed deep neural network to discriminate between Normal and Murmur class. The proposed method was evaluated on a large dataset using 5-fold cross-validation, resulting in a sensitivity and specificity of 96±0.6% and 100±0% respectively and F1 Score of 98±0.3%.

Referring now to the drawings, and more particularly to FIGS. 1 through 4, where similar reference characters denote corresponding features consistently throughout the figures, there are shown preferred embodiments and these embodiments are described in the context of the following exemplary system and/or method.

FIG. 1 illustrates an exemplary block diagram of a neural network architecture system 100 for classifying heart sound signals (HSS) in accordance with an embodiment of the present disclosure. The neural network architecture system 100 may also be referred as 'a system' and interchangeably used hereinafter. In an embodiment, the system 100 includes one or more processors 104, communication interface device(s) or input/output (I/O) interface(s) 106, and one or more data storage devices or memory 102 operatively coupled to the one or more processors 104. The one or more processors 104 may be one or more software processing modules and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the device 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment a database 108 can be stored in the memory 102, wherein the database 108 may comprise, but are not limited to information pertaining to heart sound signals (e.g., PCG signals), Spectrogram and MFCC features, weight(s) and/or bias(es) associated with each layer of the neural network architecture system 100, learning pattern/behavior, training data that is applied on test signal (or test heart sound signal), probabilities, and the like. In an embodiment, the memory 102 may store one or more technique(s) (e.g., filtering technique(s), feature extraction technique(s)), learning technique(s), classification technique(s), and the like) which when executed by the one or more hardware processors 104 to perform the methodology described herein. The memory 102 further comprises a plurality of deep neural networks (e.g., Recurrent Neural Network based Bidirectional Long Short-Term Memory (BiLSTM) and Convolutional Neural Network (CNN)) and other network layers as described below which when executed by the one or more hardware processors 104 perform the methodology (or methodologies) described herein.

Figure 2:
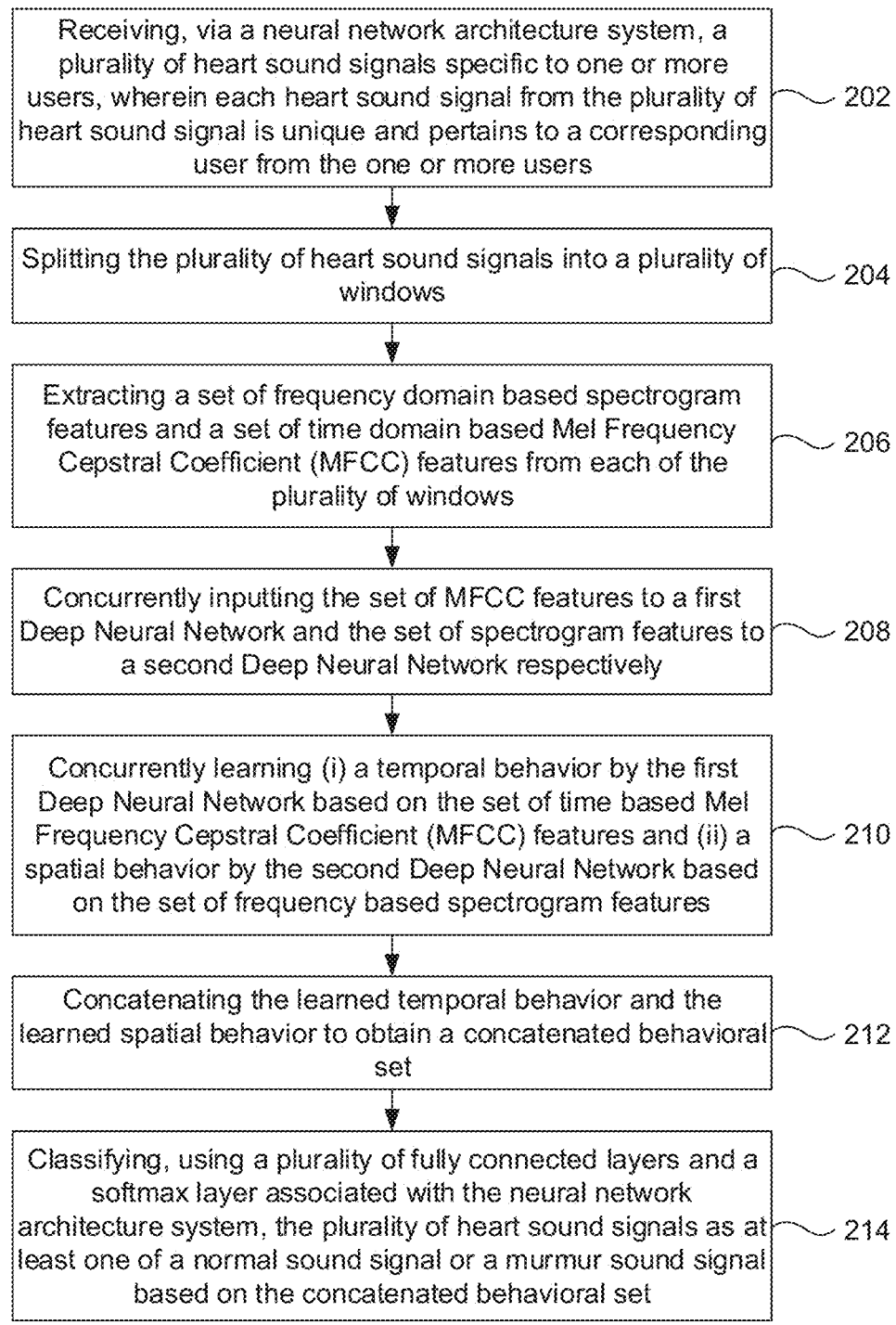
FIG. 2 illustrates an exemplary flow diagram of a method of parallel implementation of deep neural networks for classifying heart sound signals using the system of FIG. 1 in accordance with an embodiment of the present disclosure.

FIG. 2, with reference to FIG. 1, illustrates an exemplary flow diagram of a method of parallel implementation of deep neural networks for classifying heart sound signals using the system 100 of FIG. 1 in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 as depicted in FIG. 1, and the flow diagram. In an embodiment of the present disclosure, at step 202, the one or more hardware processors 104 receive, via the neural network architecture system 100, a plurality of heart sound signals specific to one or more users. Each heart sound signal from the plurality of heart sound signal is unique and pertains to a corresponding user from the one or more users. In an embodiment of the present disclosure, three publicly available heart sound dataset including:

(1) D1: 'Heart Sound and Murmur Library' 2 by University of Michigan (e.g., refer 'http://www.med.umich.edu/lrc/psb_open/html/repo/primer_heartsound/primer_heartsound.html')

(2) D2: 'Classifying Heart Sounds Challenge' 3 by Pattern Analysis, Statistical Modelling and Computational Learning (PASCAL) (e.g., refer 'http://www.peterjbentley.com/heart-challenge/').

(3) D3: 'Physionet Challenge' 2016 dataset4 by Computing in Cardiology (e.g., refer 'https://www.physionet.org/challenge/2016/')

Dataset D1 contained in total 23 recordings having various abnormal heart sound(s) out of which 14 were murmur recordings while remaining 9 were the normal category. Dataset D2 contained in total 585 annotated recordings, out of which 129 were labeled as murmurs (which includes 29 noisy data). Remaining 456 recordings (with 120 noisy data) were labeled normal heart sound which includes recording with artifacts, extra systole, extra heart sound (S3, S4, and Clicks) and normal. To further enhance the dataset(s), the present disclosure considered D3 with 3240 data (normal and abnormal) collected from patients around the world having various pathological conditions.

However, the present disclosure has considered only normal class 2575 data (including 186 noisy) and has discarded abnormal (665 recordings) heart sound from D3. As an abnormal class in this dataset includes patients recordings having both heart valve defects (including murmur sound) and coronary artery disease (CAD), and Physionet does not provide sub-classification for these recordings.

Figure 3A:
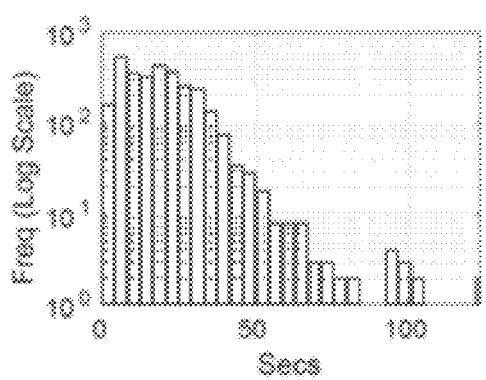
FIG. 3A depicts a histogram illustrating length of recordings of Normal class of heart sound signals in accordance with an embodiment of the present disclosure.
Figure 3B:
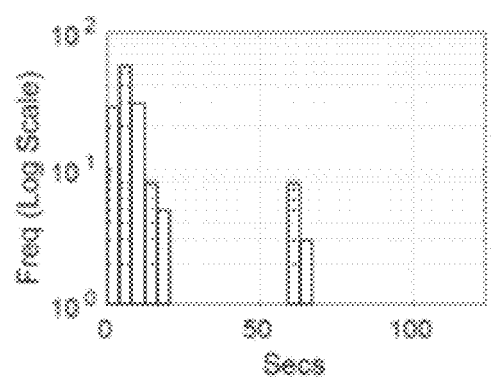
FIG. 3B depicts a histogram illustrating length of recordings of Murmur class of heart sound signals in accordance with an embodiment of the present disclosure.

Therefore, combining above datasets, the present disclosure created a single pool of data having 143 murmur recordings (14 from D1 and 129 from D2) and 3040 normal recordings (9 from D1, 456 from D2 and 2575 from D3). The sampling frequency of dataset was maintained at 2000 Hz. The data length of recordings ranges from less than a second to just above 123 seconds as depicted in FIG. 3. More specifically, FIGS. 3A-3B, with reference to FIGS. 1-2, depict a graphical representation illustrating Histogram of length of recordings of Normal and Murmur class of heart sound signals in accordance with an example embodiment of the present disclosure. More particularly, FIG. 3A depicts a histogram illustrating length of recordings of Normal class of heart sound signals in accordance with an embodiment of the present disclosure. FIG. 3B depicts a histogram illustrating length of recordings of Murmur class of heart sound signals in accordance with an embodiment of the present disclosure.

The present disclosure had created a (challenging) dataset in terms of sensor(s) diversity, different demographics, various location of recordings, different pathological conditions (Physionet data were collected from ICU/CCU (or Intensive Care Unit/Coronary Care Unit)), the variation of age and Body Mass Index (BMI) of subjects, variety of noises (ambiance, motion artifacts), varying sampling frequencies, and class imbalance. Therefore, the present disclosure and associated systems and methods pursue a generalize classifier learner over the dataset(s), where deep filters and long-term dependency aggregated by the proposed Deep Neural Network (DNN) architecture system 100 learns highly correlated features with class(es) and are sensor and noise independent.

Referring to step 204, in an embodiment of the present disclosure, the one or more hardware processors 104 split the plurality of heart sound signals into a plurality of windows. In other words, each heart sound signal is split/divided into one or more windows (e.g., time analysis windows or time windows). Each window from the plurality of windows is of a fixed time duration (e.g., say 4 seconds window). The window duration is configurable and may vary depending implementation of the system 100 in one or more various environments (e.g., IoT/cloud computing environment, and the like).

In the present disclosure, due to variation in the length of recordings, sequences (heart sound signals) are segmented (or split) into non-overlapping chunks of 4 seconds length each. The analogy behind this 4 seconds duration segmentation/split is to focus on the minute and deep feature to understand murmur rather than learning very long-term dependency which is independent of the proposed disclosure (e.g., Heart Rate Variability and breathing effect). Residual sequences of very short length (<2 sec) may not guarantee to provide sufficient murmur information and are thus removed from the data pool, whereas others are padded with trailing zero. After segmentation/splitting, 10,892 instances of data out of which 272 belong to murmur class (class ratio nearly equals 39:1 normal:murmur).

Referring to step 206, in an embodiment of the present disclosure, the one or more hardware processors 104 extract a set of frequency domain based spectrogram features and a set of time domain based Mel Frequency Cepstral Coefficient (MFCC) features from each of the plurality of windows. It is noted that Deep Learning has provided many tools for automatic feature extraction based on raw data and its annotation, for example, Autoencoder, and Convolutional Neural Network kernels on raw signals to learn important (critical) filters. However, these work best for the spatial feature extraction of significantly high-resolution signal compared to the proposed single dimension heart sound signal(s). Therefore, in the present disclosure, features extraction is performed for the classification of signals (e.g., heart sound signals).

Prior to performing features extraction, the heart sound signals may be preprocessed to filter noise and other artefacts that may be irrelevant for classification tasks. For instance, Murmur, being a pseudo-periodic non-stationary high-frequency signal, both temporal and spatial trend(s) are required to discriminate disease(s) from normal class. This may further reduce biases towards noises (ambiance and motion artifact) which are relatively aperiodic and of varying frequency spectra. Before feature extraction, the present disclosure and systems and methods associated thereof apply low pass followed by high pass filters with cutoff frequencies 500 Hz ('Hz' is also referred as 'Hertz') and 25 Hz respectively on the plurality of heart sound signals (e.g., can be referred as pre-processing technique). Further, noisy spike(s) in the heart sound signal are also removed using method(s) described in conventional art (e.g., refer 'Samuel E Schmidt, CGCTESJJ Holst-Hansen, Claus Graff, Egon Toft, and Johannes J Struijk. 2010. Segmentation of heart sound recordings by a duration-dependent hidden Markov model. Physiological measurement 31, 4 (2010), 513.'). The present disclosure and associated systems and methods thereof utilize acoustic features: Mel filter based Mel-Frequency Cepstral Coefficients (MFCC), a well-known technique in speech processing, and short-term Fourier transform based spectrogram to find the time-dependent and visual signature of the signal(s) respectively. In the present disclosure, the expression 'signal' and 'heart sound signal' may be interchangeably used hereinafter. The following technique was implemented by the systems and methods of the present disclosure to compute (or extract) the above features:

Extraction of frequency domain based Spectrogram features:
1. Heart sound signals were divided into small windows of length 'x' (e.g., say 128 milliseconds) and step size of 'y' (e.g., say 64 milliseconds)
2. On each window, Fast Fourier Transform (FFT) is applied with a Hamming window of the length of 'z' (e.g., where value of 'z' is 128)
3. This resulted to spectrogram image of dimension [m×n] wherein value of 'm' was 65 and value of 'n' was 61 for a 4 sec heart sound.

Extraction of time domain based Mel Frequency Cepstral Coefficient (MFCC) Cepstrogram features:
1. Heart sound signals were divided into small windows (with window index i) of length 'a' (e.g., value of 'a' is 25 milliseconds) and step size of 'b' (e.g., where value of 'b' is 10 milliseconds)
2. On each window Discrete Fourier Transform (DFT) $D_i(k)$ ($k \in [1, K]$, where K is length of DFT are applied with Hamming window of length of 'c' (e.g., value of 'c' is 50)
3. Spectral power estimate $P_i(k)$ is computed on the DFT signal for every window.
4. 26 Filterbanks channels of triangular band-pass filters (with cutoff frequency range [X, Y] wherein value of X is 70 and Y is 500 respectively followed by log transformation is applied to $P_i(k)$
5. Discrete Cosine Transform is finally applied to compute MFCCs features with 13 coefficients for each window i.
6. Cepstral feature of each window are combined to get Cepstrogram sequence of dimension [M×N] where value of M is 13 and N is 398 respectively for a 4 second heart sound signal.

Figure 4:
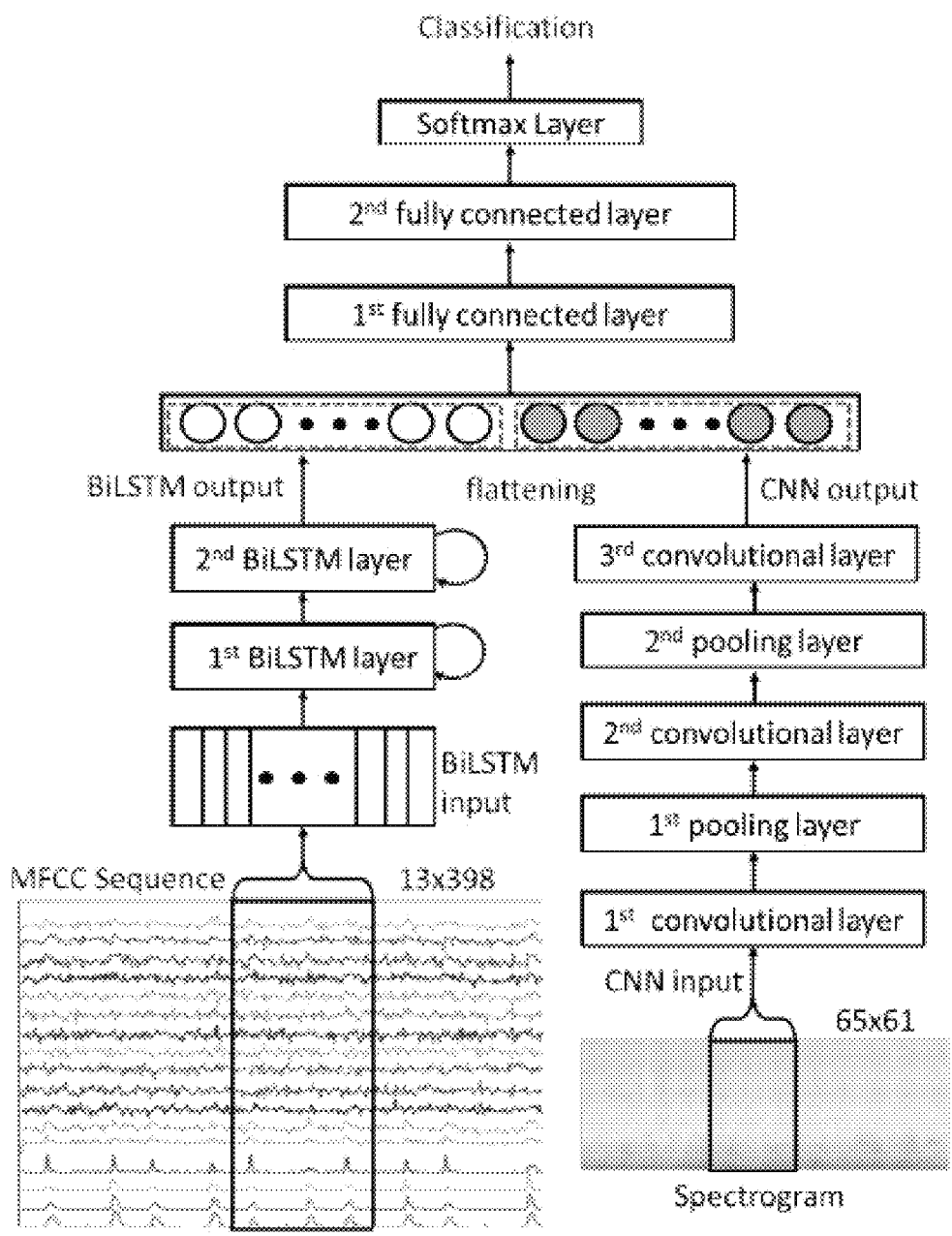
FIG. 4 depict an exemplary block diagram of the system of FIG. 1 illustrating a parallel implementation of Deep Neural Networks for classifying heart sound signals in accordance with an embodiment of the present disclosure.

Referring to step 208, in an embodiment of the present disclosure, the one or more hardware processors 104 concurrently input the set of MFCC features to a first Deep Neural Network and the set of spectrogram features to a second Deep Neural Network respectively, wherein the first Deep Neural Network may be referred as 'first DNN') and the second Deep Neural Network may be referred as 'second DNN'). In the present disclosure, two parallel deep neural networks are proposed, namely, Recurrent Neural Network based Bidirectional Long Short-Term Memory (BiLSTM) and Convolutional Neural Network (CNN). An exemplary schema of the proposed neural network architecture system is depicted in FIG. 4. More specifically, FIG. 4, with reference to FIGS. 1 through 3B, depict an exemplary block diagram of the system 100 of FIG. 1 illustrating a parallel implementation of Deep Neural Networks for classifying heart sound signals in accordance with an embodiment of the present disclosure.

In an embodiment of the present disclosure, at step 210, the first Deep Neural Network learns a temporal behavior based on the set of time based Mel Frequency Cepstral Coefficient (MFCC) features and the second Deep Neural Network learns a spatial behavior based on the set of frequency based Spectrogram features. In an embodiment, the first Deep Neural Network and the second Deep Neural Network are different from each other. For instance, the first Deep Neural Network comprises a Recurrent Neural Network, and the second Deep Neural Network comprises a Convolution Neural Network as described above. Each of the first DNN and the second DNN may further comprise other network layers that may be utilized to perform the methodology described herein, in one example embodiment.

LSTM (or RNN) contains hidden layers with self-recurrent weights which enables the cell (nodes) in the memory block to retain past information. This inference of prior information is used for future estimation; thus LSTM is famous for extracting the temporal pattern of the sequence. Bi-directional LSTM (BiLSTM) is the modified LSTM which has a bidirectional flow to process the sequence in both forward and backward direction and fed forward to the output layer. Two hidden layers present in BiLSTM computes hidden sequences both in forward and backward direction and updates the output layer by using backward layer (from last time step to the first) and forward layer (from first to last time step). In the proposed system, the first DNN (e.g., BiLSTM) learns the temporal trend of MFCC's sequences of the heart sound signals.

Convolutional layer performs 2-dimensional convolution between the spectral image and the trained filters. To learn the different aspect of the features, numbers of filter channels are used. Thus, in the present disclosure when N different filters are applied to the spectrogram, N output filtered images $F_i$ ($i \in N$) are computed in the convolutional layer. The filtered images $F_i$ are forwarded to the pooling layer which evaluates the sub-segments of $F_i$ and compute maximum value which down samples the image. This spatial down sampling ensures the most dominant feature in the sub-region is extracted.

In an embodiment of the present disclosure, at step 212, the learned temporal behavior and the learned spatial behavior are concatenated (or linked together) to obtain a concatenated behavioral set. In other words, the concatenation may be performed by the system 100 or the one or more hardware processors 104 (or by one or more layers (e.g., a final pooling layer) of the system 100 as depicted in FIG. 4). In other words, as depicted in FIG. 4, in the final pooling layer, the resized outputs (outputs from the first DNN and the second DNN) are flattened/concatenated (e.g., refer dotted blocks indicating BiLSTM output and CNN output) in order to connect with the subsequent fully connected layers. More specifically, outputs from the first DNN and the second DNN are merged by flattening and/or concatenating following fully connected layers with common loss back-propagation path. The LSTM layers utilize the sequence of acoustic MFCCs feature, while the CNN layers use spectral images as input.

In an embodiment of the present disclosure, at step 214, the plurality of heart sound signals are classified as one of a normal sound signal or a murmur sound signal based on the concatenated behavioral set. This classification is performed using the fully connected layers (e.g., $1^{st}$ fully connected layer and $2^{nd}$ fully connected layer) and a softmax layer associated with the neural network architecture system 100 depicted in FIG. 4. During the learning of temporal behavior and spatial behavior of the extracted features associated with the heart sound signals, one or more weights and/or one or more biases pertaining to layer(s) of the neural network architecture system 100 are also learnt. In others words, layer(s) comprises layers of the first DNN and the DNN respectively, the plurality of fully connected layers and the softmax layer as depicted in FIG. 4. The above steps 202 till 214 attribute to training of the neural network architecture system 100. Upon training the neural network architecture system 100, training data is accumulated which is utilized along with the learnt weight(s) and/or bias(es) for classification of test heart sound signal(s).

In order to train the proposed system 100 (e.g., the neural network architecture system 100), two sets of features (Spectrogram and MFCC sequence) of every instance are fed simultaneously in the same order in every iteration of the epoch. Therefore, two ordered datasets are maintained for each corresponding features accordingly. For robust performance evaluation, the present disclosure performed 5-fold cross-validation over 10,892 data. However, due to the predominance of class imbalance (nearly 39:1 normal:murmur as quoted earlier), training would be bias towards majority class. Therefore, the minor class in training data was augmented in each fold independently by upsampling (repeating minor class) to create balanced class training set, however, test data in every fold was left as it is. Moreover, it was ensured by the present disclosure that data segments of the same recording (before segmentation) were not present in both train and test in any of the folds.

In a nutshell, in the BiLSTM architecture of the proposed system 100, input sample consisted 398 frames with 13-dimensional MFCC features, in an example embodiment. The network has two BiLSTM layers with 128 BiLSTM units each and one feed-forward layer with 128 ReLU units similar to CNN output as depicted in FIG. 4. Dropout was applied to all the layers with keeping probability of 80%. Parallel BiLSTM and CNN structure was built and their outputs (128 each) were combined to form a single fully connected layer with 256 units. Second fully connected layer has 128 units which is connected to output layer containing two softmax nodes identical to the number of class (Normal and Murmur). This combined structure was then trained over the dataset explained above. All the network(s) were trained using cross-entropy error as the loss function. In each epoch, 128 mini-batches were set in random order (however with same seed over two feature sets to maintain uniformity in order). Learning rate was kept 1E-3 throughout training.

The proposed CNN architecture system 100 comprises three convolutional layers, two max-pooling layers, and a fully connected layer to flatten the output of CNN. The input to this CNN was 65×61 spectrogram features as depicted in FIG. 4. In the first convolutional layer, the input was convolved with 4 filters of size 3×3, in an example embodiment. Batch normalization followed by Rectified Linear Unit (ReLU) activation function was applied on the output of the convolutional filter. First max-pooling layer summarizes and reduces the size of filters using 2×2 kernel. Similarly, two subsequent convolutional layers convolve output of max-pooling layers using 3×3 filter followed by batch normalization and ReLU activations. Final activation output is then flattened and fed to fully connected layer with 128 units. To reduce over-fitting, L2-Regularization was used over all the layers in CNN.

Testing:

During the testing phase, the system 100 receives a test heart sound signal, wherein the test heart sound signal may be pre-processed for noise and artefacts removal (as done during the training phase). One or more spectrogram features and one or more MFCC features are then extracted from the test heart sound signal. The learned one or more weights and one or more biases from the training phase are applied on the one or more spectrogram features and the one or more MFCC features (that are extracted in previous step) to obtain a plurality of probabilities pertaining to the test heart sound signal. The test heart sound signal is then classified as one of the normal sound signal or the murmur sound signal based on the probabilities. For instance if a first probability value is 0.8 and a second probability value of 0.2 (i.e., 1−0.8), then both are compared to determine which is highest or lowest. The probability that is of highest value is used to determine the class. In this case, the test heart sound signal can be classified as Normal heart sound signal.

Results and Observations:

A set of performances measures (e.g., Sensitivity (the portion of normal class predicted normal), Specificity (the portion of murmur class predicted murmur), and F1 Score of Normal class) is presented over 5-fold cross-validation as shown in below Table 1. Performance of the proposed neural network architecture system 100 (e.g., (BiLSTM+CNN)) and individual CNN and BiLSTM networks too which were trained and tested independently is provided. As can be seen that CNN and BiLSTM networks are slightly biased towards Murmur and Normal class respectively. This is because CNN network learns visual filters for discrimination; however, it faces difficulties differentiating noisy data of Normal class and Murmur. On the other hand, BiLSTM learns the long-term repetitive patterns of the principle heart sound (S1 and S2) of Normal class but fails to discriminate few instances of Murmur sound which are dominant in periodicity. Therefore, when both networks are combined (BiLSTM+CNN) in parallel as proposed and implemented by the neural network architecture system 100, it is observed the system 100 learns visual as well as the time-dependent aspect of the signal and are a better place to discriminate the classes.

TABLE 1

| Neural Network architecture type | Sensitivity | Specificity | F1 Score |
| --- | --- | --- | --- |
| CNN | 0.8704 ± 0.0137 | 1 ± 0 | 0.9307 ± 0.0079 |
| BiLSTM | 0.9714 ± 0.0079 | 0.8549 ± 0.0636 | 0.9835 ± 0.0042 |
| CNN + BiLSTM (or BiLSTM + CNN) – proposed neural network architecture system | 0.9609 ± 0.0061 | 1 ± 0 | 0.9801 ± 0.0032 |

The results as depicted in above Table 1 show that proposed neural network architecture system achieves 100% Specificity and 96% Sensitivity, a significant boost when compared with existing art/techniques. The major positive point of the proposed system 100 lies behind the fact that it does not depends on beat (heart cycle from S1 to next occurring S1) segmentation technique, which has its own sensitivity and specificity, and is independent of onset estimation.

To learn the instantaneous (spatial) and time-varying dependency of the murmur sound, the present disclosure implemented the deep learning architecture to be trained on the heart sound signal(s). The present disclosure enables the system 100 to utilize CNN layers to learn the spatial (presence of different frequencies component) filters from the Spectrogram feature of the signal(s), while RNN based bidirectional LSTM layer is used to learn time-varying component of the signal(s) from MFCC features of the signal(s). Using these features (Spectrogram and MFCC) as an input source to CNN and RNN respectively enables the system 100 for classification of heart sound signals or detect the heart sound signal (e.g., test signal) as normal or murmur signal. The CNN layers learn the presence of the high-frequency component of murmur in a window, however, its occurrence is also tracked with respect to time. Therefore, RNN (which has sequential properties) is used which iterates past events and remembers its sequence. This helps to retain prior knowledge of the signal (e.g., heart sound signal) and also the current state scenario to judge (or determine) the presence of murmur accurately. MFCC sequence features (also referred as 'time based Mel Frequency Cepstral Coefficient (MFCC) features') are introduced to RNN because MFCC approximates the human auditory system's response more closely than the linearly-spaced frequency bands—this type of frequency warping can allow for better representation of sound signal (e.g., heart sound signal). The analogy behind using MFCC is similar to as of a doctor/physician/medical expert/medical professional would listen and judge (or determine) the heart sound (signal). Additionally, visual assistance (Spectrogram) would make the model/system 100 more robust for murmur detection. These two sets of layers (RNN layers and CNN layers) in parallel and the output of both are concatenated to classify the heart sound signal into normal/murmur heart sound signal. The ability of the system 100 to perform short window analysis (e.g., 4 seconds splitting and analysis), enables prediction of the heart sound signal as normal/murmur in just 4 seconds. Based on domain understanding, and analysis it was also found that spatial occurrence of the abnormal sound is not enough to classify it to murmur, and hence temporal information is also considered to find its relative positioning compared to primary heart sounds (S1 and S2) which is not considered or implemented by conventional systems and methods.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
receiving, via a neural network architecture system, a plurality of heart sound signals specific to one or more users, wherein each heart sound signal from the plurality of heart sound signal is unique and pertains to a corresponding user from the one or more users;
splitting the plurality of heart sound signals into a plurality of windows;

extracting a set of frequency domain based spectrogram features and a set of time domain based Mel Frequency Cepstral Coefficient (MFCC) features from each of the plurality of windows;

concurrently inputting the set of MFCC features to a first Deep Neural Network and the set of spectrogram features to a second Deep Neural Network respectively;

concurrently learning (i) a temporal behavior by the first Deep Neural Network based on the set of time based Mel Frequency Cepstral Coefficient (MFCC) features and (ii) a spatial behavior by the second Deep Neural Network based on the set of frequency based spectrogram features;

concatenating the learned temporal behavior and the learned spatial behavior to obtain a concatenated behavioral set; and classifying, using a plurality of fully connected layers and a softmax layer associated with the neural network architecture system, the plurality of heart sound signals as at least one of a normal sound signal or a murmur sound signal based on the concatenated behavioral set, wherein during the learning one or more weights and biases of (i) one or more layers of the first DNN and the DNN respectively, (ii) the plurality of fully connected layers and the softmax layer of the neural network architecture system are learnt.

2. The processor implemented method of claim 1, further comprising:

receiving, via the neural network architecture system, a test heart sound signal;

extracting one or more spectrogram features and one or more MFCC features from the test heart sound signal;

applying the learned one or more weights and biases on the one or more spectrogram features and the one or more MFCC features to obtain a plurality of probabilities pertaining to the test heart sound signal; and classifying, based on the plurality of probabilities, the test heart sound signal as the normal sound signal or a murmur sound signal.

3. The processor implemented method of claim 1, wherein the first Deep Neural Network and the second Deep Neural Network are different from each other.

4. The processor implemented method of claim 1, wherein the first Deep Neural Network comprises a Recurrent Neural Network.

5. The processor implemented method of claim 1, wherein the second Deep Neural Network comprises a Convolution Neural Network.

6. The processor implemented method of claim 1, wherein each of the plurality of windows is of a fixed time duration.

7. A Neural Network architecture system, comprising:
a memory storing instructions;
one or more communication interfaces; and
one or more hardware processors coupled to the memory via the one or more communication interfaces, wherein the one or more hardware processors are configured by the instructions to:
receive a plurality of heart sound signals specific to one or more users, wherein each heart sound signal from the plurality of heart sound signal is unique and pertains to a corresponding user from the one or more users;
split the plurality of heart sound signals into a plurality of windows;
extract a set of frequency domain based spectrogram features and a set of time domain based Mel Frequency Cepstral Coefficient (MFCC) features from each of the plurality of windows;

concurrently input the set of MFCC features to a first Deep Neural Network and the set of spectrogram features to a second Deep Neural Network respectively, wherein the first Deep Neural Network and the second Deep Neural Network are configured by the instructions to:
concurrently learn a temporal behavior based on the set of time based Mel Frequency Cepstral Coefficient (MFCC) features and (ii) a spatial behavior based on the set of frequency based spectrogram features respectively;
concatenate the learned temporal behavior and the learned spatial behavior to obtain a concatenated behavioral set; and
classify, using a plurality of fully connected layers and a softmax layer associated with the neural network architecture system, the plurality of heart sound signals as at least one of a normal sound signal or a murmur sound signal based on the concatenated behavioral set, wherein during the learning one or more weights and biases of (i) one or more layers of the first DNN and the DNN respectively, (ii) the plurality of fully connected layers and the softmax layer of the neural network architecture system are learnt.

8. The system of claim 7, wherein the neural network architecture system is further configured by the instructions to:
receive a test heart sound signal;
extract one or more spectrogram features and one or more MFCC features from the test heart sound signal;
apply the learned one or more weights and biases on the one or more spectrogram features and the one or more MFCC features to obtain a plurality of probabilities pertaining to the test heart sound signal; and
classify, based on the plurality of probabilities, the test heart sound signal as the normal sound signal or a murmur sound signal.

9. The system of claim 7, wherein the first Deep Neural Network and the second Deep Neural Network are different from each other.

10. The system of claim 7, wherein the first Deep Neural Network comprises a Recurrent Neural Network.

11. The system of claim 7, wherein the second Deep Neural Network comprises a Convolution Neural Network.

12. The system of claim 7, wherein each of the plurality of windows is of a fixed time duration.

13. One or more non-transitory machine readable information storage mediums comprising one or more instructions which when executed by one or more hardware processors cause:
receiving, via a neural network architecture system, a plurality of heart sound signals specific to one or more users, wherein each heart sound signal from the plurality of heart sound signal is unique and pertains to a corresponding user from the one or more users;
splitting the plurality of heart sound signals into a plurality of windows;
extracting a set of frequency domain based spectrogram features and a set of time domain based Mel Frequency Cepstral Coefficient (MFCC) features from each of the plurality of windows;
concurrently inputting the set of MFCC features to a first Deep Neural Network and the set of spectrogram features to a second Deep Neural Network respectively;
concurrently learning (i) a temporal behavior by the first Deep Neural Network based on the set of time based Mel Frequency Cepstral Coefficient (MFCC) features and (ii) a spatial behavior by the second Deep Neural Network based on the set of frequency based spectrogram features;

concatenating the learned temporal behavior and the learned spatial behavior to obtain a concatenated behavioral set; and classifying, using a plurality of fully connected layers and a softmax layer associated with the neural network architecture system, the plurality of heart sound signals as at least one of a normal sound signal or a murmur sound signal based on the concatenated behavioral set, wherein during the learning one or more weights and biases of (i) one or more layers of the first DNN and the DNN respectively, (ii) the plurality of fully connected layers and the softmax layer of the neural network architecture system are learnt.

14. The one or more non-transitory machine readable information storage mediums of claim 13, wherein the instruction which when executed by the one or more hardware processors further cause:

receiving, via the neural network architecture system, a test heart sound signal;

extracting one or more spectrogram features and one or more MFCC features from the test heart sound signal;

applying the learned one or more weights and biases on the one or more spectrogram features and the one or more MFCC features to obtain a plurality of probabilities pertaining to the test heart sound signal; and classifying, based on the plurality of probabilities, the test heart sound signal as the normal sound signal or a murmur sound signal.

15. The one or more non-transitory machine readable information storage mediums of claim 13, wherein the first Deep Neural Network and the second Deep Neural Network are different from each other.

16. The one or more non-transitory machine readable information storage mediums of claim 13, wherein the first Deep Neural Network comprises a Recurrent Neural Network.

17. The one or more non-transitory machine readable information storage mediums of claim 13, wherein the second Deep Neural Network comprises a Convolution Neural Network.

18. The one or more non-transitory machine readable information storage mediums of claim 13, wherein each of the plurality of windows is of a fixed time duration.

* * * * *